United States Patent [19]

Phillips et al.

[11] Patent Number: 4,458,096

[45] Date of Patent: Jul. 3, 1984

[54] PROCESS FOR THE PRODUCTION OF ETHYLENE AND PROPYLENE

[75] Inventors: David J. Phillips; Jerome L. Glazer, both of Allentown, Pa.

[73] Assignee: Air Products and Chemicals, Inc., Allentown, Pa.

[21] Appl. No.: 498,360

[22] Filed: May 26, 1983

[51] Int. Cl.$^3$ ............... C07C 5/333; C07C 11/04; C07C 11/06

[52] U.S. Cl. ............... 585/302; 585/304; 208/80; 208/130

[58] Field of Search ............ 208/80, 130; 585/302, 585/304, 652

[56] References Cited

U.S. PATENT DOCUMENTS

| | | | |
|---|---|---|---|
| 1,524,355 | 1/1925 | Haynes et al. | 585/302 |
| 2,137,825 | 11/1938 | Sullivan | 585/304 |
| 2,350,628 | 6/1944 | Matuszak | 585/302 |
| 3,005,857 | 10/1961 | Steinhoffer et al. | 208/130 |
| 3,113,984 | 12/1963 | Gossehin et al. | 260/677 |
| 3,161,696 | 12/1964 | Eder et al. | 585/652 |
| 3,345,285 | 10/1967 | Hutto et al. | 585/304 |
| 3,474,156 | 10/1969 | Bloch | 208/80 |
| 3,475,510 | 10/1969 | Newman et al. | 208/130 |
| 3,487,121 | 12/1969 | Hallee | 585/652 |
| 3,617,498 | 11/1971 | Kittren | 585/302 |
| 3,624,176 | 11/1971 | Lhonore | 585/652 |
| 3,641,182 | 2/1972 | Box, Jr. et al. | 260/680 R |
| 3,647,682 | 3/1972 | Rabo et al. | 208/120 |
| 3,708,552 | 1/1973 | Kunhi et al. | 208/53 |
| 3,720,600 | 3/1973 | Mansfield et al. | 208/47 |
| 3,764,634 | 10/1973 | Ozawa et al. | 585/648 |
| 3,880,776 | 4/1975 | Box, Jr. et al. | 252/466 PT |

FOREIGN PATENT DOCUMENTS

| | | | |
|---|---|---|---|
| 552806 | 2/1958 | Canada | 208/130 |
| 2064576 | of 1981 | United Kingdom | 208/130 |

*Primary Examiner*—Delbert E. Gantz
*Assistant Examiner*—Helane E. Maull
*Attorney, Agent, or Firm*—Mark L. Rodgers; E. Eugene Innis; James C. Simmons

[57] ABSTRACT

A process is described for producing ethylene and propylene in high selectivity from feed streams containing ethane and propane. The process involves separating the feed into ethane and propane fractions and subsequently cracking the ethane fraction to produce ethylene and dehydrogenating the propane fraction to produce propylene. The fractions are then combined and purified, and the ethylene and propylene products are recovered. Any unreacted ethane or propane is recycled back to the cracking or dehydrogenation units respectively.

5 Claims, 1 Drawing Figure

PROCESS FOR THE PRODUCTION OF ETHYLENE AND PROPYLENE

TECHNICAL FIELD OF THE INVENTION

This invention relates to the production of ethylene and propylene from gas streams containing ethane and propane.

BACKGROUND OF THE INVENTION

There are many well known processes for the production of ethylene and propylene from feedstocks containing saturated hydrocarbons. One such process is thermal or steam cracking. By this method, a hydrocarbon feed stream is heated in an externally fired reactor to a temperature to effect conversion of a portion of the feedstream to gaseous unsaturated hydrocarbons. A particular example of this type of process is described in U.S. Pat. No. 3,764,634. In this process a hydrocarbon feedstock is introduced to an externally heated tubular cracking furnace together with a particulate abrasive material. The mixture is heated to a temperature in the range from about 600° to about 900° C. to convert a substantial portion of the feedstock to gaseous, unsaturated hydrocarbons. The resulting fluidized vaporous reaction mixture containing suspended abrasive particles is circulated through the cracking furnace to a quenching zone, whereby the scouring action of the abrasive particles prevents the deposition of by-product coke on the inner surface of the furnace.

Additional hydrocarbon steam cracking methods are described in U.S. Pat. Nos. 3,720,600 and 3,708,552.

A second method of producing ethylene and propylene from ethane and propane is by dehydrogenation. U.S. Pat. No. 3,113,984 describes a method for the dehydrogenation of hydrocarbons to produce olefins having from three to five carbon atoms per molecule from a feedstock having the same number of carbon atoms per molecule. According to this process, a reactant gas stream consisting of a hydrocarbon feedstock, steam, oxygen and inert gas is produced. The volume ratios of the hydrocarbon feed, steam and oxygen in the reactant stream are controlled within a certain prescribed range. The reactant gas stream is passed though a bed of activated charcoal granules to produce a product stream containing olefins having the same number of carbon atoms as the feedstock.

U.S. Pat. No. 3,647,682 discloses a dehydrogenation process for producing olefins from petroleum feedstocks rich in saturated hydrocarbons using zeolitic molecular sieve catalysts. This process provides for catalyticaly cracking paraffinic hydrocarbons to produce ethylene and propylene.

There are also a number of other dehydrogenation processes which are used in the art. In one process, fresh feed is mixed with unconverted hydrocarbon recycle feed and hydrogen-rich recycle gas and converted to the desired product over a noble metal catalyst such as platinum over alumina, at about atmospheric pressure.

Other processes use multiple metal promoted catalysts over highly calcined supports. Fresh feed and unconverted hydrocarbon recycle is passed over the catalyst at pressures from about 1 to 8 atmospheres and temperatures above about 475° C. in the presence of at least 2 to 3 moles of steam per mole of feed for dilution. Examples of dehydrogenation processes using metal promoted catalysts are described in U.S. Pat. Nos. 3,641,182 and 3,880,776.

Still another process uses a Chromia catalyst under vacuum and at a temperature effective for dehydrogenating the propane.

BRIEF SUMMARY OF THE INVENTION

We have found an efficient process for producing ethylene and propylene in high selectivity from feed streams containing ethane and propane. In accordance with our invention, a feed stream is separated into an ethane fraction and a propane fraction. The ethane fraction is passed through a cracking unit at a temperature ranging from about 750° to 930° C., thereby forming an ethylene-rich stream.

The propane fraction is passed through a dehydrogenation unit over a suitable catalyst at a temperature from about 425° to 815° C., thereby forming a propylene-rich stream. The propylene-rich stream is then compressed, if necessary, to a pressure about equal to that of the ethylene-rich stream. The two streams are combined and compressed and cooled. Ethylene and propylene are recovered from the resulting stream by low temperature fractionation. Finally, any unreacted ethane and propane are recycled back to the steam cracking and dehydrogenation units respectively.

While there are many methods in the art for producing ethylene and propylene from an ethane and propane feed stream, the present invention has the advantage of selectively producing a greater amount of ethylene and propylene from the same amount of feedstock. The combined product selectivity of the present invention is also not greatly affected by the ethylene/propylene product ratio. In addition, the ability to recycle unreacted ethane and propane makes this invention even more advantageous. Finally, the use of catalytic dehydrogenation for the propane fraction results in a propylene-rich stream that contains very little acetylene, methyl acetylene and propadiene, thereby eliminating or greatly reducing in severity the need for hydrotreating during the compression and cooling or product recovery steps.

DETAILED DESCRIPTION OF THE INVENTION

Figure 1:
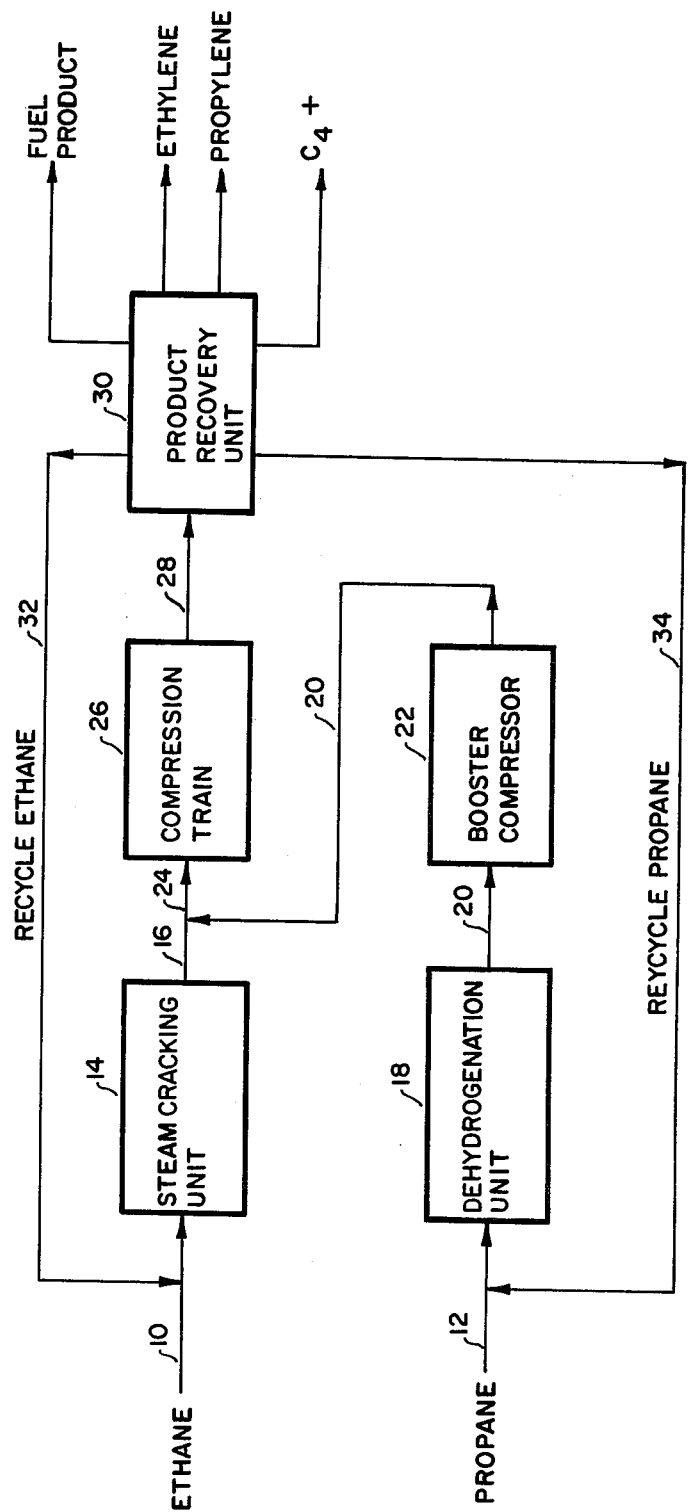
FIG. 1 is a schematic flow diagram of the present invention.

In accordance with the present invention a feedstream rich in ethane and propane is separated into an ethane fraction and a propane fraction if said fractions are not already separate. The original feed can be any feed rich in $C_2$ and $C_3$ hydrocarbons, however, the present invention is especially adaptable to feeds from natural gas wells, from associated off gases of petroleum production, or from petroleum refining or other petroleum chemical operations.

As shown in FIG. 1 the ethane fraction indicated by arrow 10 is passed through a steam cracking unit 14 at a temperature in the range of about 750°–930° C. This cracking treatment is effective to convert the ethane fraction into an ethylene-rich stream, indicated by arrow 16, typically containing at least 50% dry volume ethylene. Typically this product is at a pressure of about 1 atmosphere. Steam cracking unit 14 can be any cracking apparatus know in the art which is effective for converting ethane to ehtylene, however, preferably it is one or more externally fired tubular reactors with short residence times. Dilution steam is used in cracking unit 14 to reduce hydrocarbon partial pressure and inhibit the build up of coke in the unit. Since little or no propane is introduced into the steam cracker 14, less undesirable by-products such as acetylene, methyl-acetylene, and propadiene are produced. This reduces or eliminates the need for hydrotreating the resulting product to remove these impurities prior to or during final product fractionation. Additionally, the cracking unit 14 produces very little propane or propylene.

The propane fraction indicated by arrow 12 is passed through a dehydrogenation unit 18 over a suitable catalyst at a temperature in the range from about 425° to 815° C. This dehydrogenation treatment is effective to convert the propane fraction into a propylene-rich stream, indicated by arrow 20, typically containing at least 30% dry volume propylene. While ethane is not introduced into the dehydrogenation unit 18, some ethane and ethylene are still produced. Any dehydrogenation technique known in the art which is capable of converting propane to propylene can be used. Preferred methods include using a noble metal or metal oxide catalyst on a calcined support.

Depending upon the type of dehydrogenation process used, the propylene-rich stream leving the dehydrogenation unit 18 may be below atmospheric pressure. If this is the case, the propylene-rich stream is passed through a booster compressor 22 where it is compressed to a pressure about equal to that of the ethylene-rich stream. The two said streams are then mixed to form a single combined ethylene/propylene stream indicated by arrow 24.

The combined ethylene/propylene stream is initially compressed and cooled in a compression train 26. During this compression and cooling step, impurities and by-products are removed, thereby producing a refined stream indicated by arrow 28. This refined stream is typically at a pressure in the range of about 28 to 38 atmospheres and temperature in the range of about 32° to 45° C. Due to the similarity in composition of the ethylene-rich stream and the propylene-rich stream, a common compression train 26 can be used for the mixture of the two streams. Also, since less acetylene, methylacetylene, and propadiene are produced, the need for hydrotreating the combined stream during the compressing and cooling or product recovery steps is greatly reduced or eliminated. The refined stream is then passed through a product recovery unit 30 where ethylene and propylene are recovered by low temperature fractionation. At least about 80 weight % of the combined initial ethane/propane stream is recovered as purified ethylene and propylene by this method. Light by-products are rejected as a fuel product, with possible separate recovery of hydrogen as a by-product, and heavier hydrocarbons are recovered for further processing or else are discarded. Unreacted ethane and/or any ethane produced from the dehydrogenation of the propane stream is recycled via conduit 32 back to the initial ethane feed stream. Unreacted propane and/or any propane produced from the cracking of the ethane fraction is recycled via conduit 34 and combined with fresh propane feed.

By integrating the product recovery system, the present invention has the advantage that ethane and ethylene produced in the dehydrogenation reaction are recovered as product or recycled to the cracking unit. If the product recovery units were built separately, this ethane and ethylene would be rejected as fuel since the small quantities would not justify their recovery. Likewise, propane produced in the cracker is recycled to the dehydrogenation unit where it is selectively converted to propylene instead of being discarded as it would be if separate recovery units were used. By combining steam cracking with catalytic dehydrogenation and integrating the recovery and product separation sections, ethylene and propylene can be produced using less feedstock. Also, since the initial feeds are segregated, propane can be kept out of the cracking unit where it would react to form lower valued products and impurities.

EXAMPLE 1

Three separate runs were made comparing the integrated system of the present invention with a system employing only a cracking unit. Conditions were controlled so as to achieve predetermined $C_2=/C_3=$ product ratios for each run. The product ratios were manipulated by holding the ethylene production constant while varying the propylene production. The feed and product rates for these runs are reported in Table 1 below.

TABLE I

| Run | 1 | | 2 | | 3 | |
|---|---|---|---|---|---|---|
| $C_2=/C_3=$ Ratio | 1.8 | | 3.1 | | 6.1 | |
| Case | $C_3$ Crkr. Only | Integrated System | $C_3$ Crkr. Only | Integrated System | $C_2/C_3$ Crkr. Only | Integrated System |
| Feed (MTPY)[1] | | | | | | |
| $C_2$ | | 336,825 | | 344,730 | 177,535 | 349,885 |
| $C_3$ | 690,900 | 222,375 | 641,766 | 126,000 | 320,885 | 63,240 |
| | 690,900 | 559,200 | 641,766 | 470,730 | 498,420 | 413,125 |
| Products (MTPY)[1] | | | | | | |
| $H_2$ | 17,175 | 37,470 | 14,800 | 33,387 | 21,560 | 30,800 |
| $C_1$ | 159,170 | 25,214 | 160,562 | 19,535 | 85,858 | 15,464 |
| $C_2=$ | 300,000 | 300,000 | 300,000 | 300,000 | 300,000 | 300,000 |
| $C_3=$ | 168,350 | 168,350 | 96,434 | 96,434 | 48,950 | 48,950 |
| Butadiene | 17,195 | 6,990 | 19,634 | 7,049 | 13,380 | 7,090 |
| $C_4$'s | 3,470 | 2,540 | 3,429 | 2,595 | 2,960 | 2,570 |
| Heavy | 25,540 | 11,576 | 46,907 | 7,730 | 25,712 | 6,250 |
| Product lost due to coke and combustion | | 7,060 | | 4,000 | | 2,001 |
| Combined $C_2=/C_3=$ Product | 67.8 | 83.8 | 61.8 | 84.2 | 70.0 | 84.5 |

TABLE I-continued

| Run | 1 | 2 | 3 |
|---|---|---|---|
| (Wt. %) | | | |

[1]Metric Tons Per Year

It can be seen from the above results that at all three product ratios, less feed is required in the integrated system than by a system using only a cracking unit. In Run 1, for example, the system using the cracking unit alone requires 131,700 MTPY of additional feed than the integrated system to produce 468,350 MTPY of $C_2=/C_3=$ in a product ratio of 1.8:1.

As the $C_2=/C_3=$ product ratio approaches 3.0, as in Run 2, the advantages of the integrated system become greater. This is because the product selectivity of the cracker alone is lowest at this ratio. Although the integrated system is most preferred when a $C_2=/C_3=$ product ratio of about 3.0 is desired, the integrated scheme is more selective than the cracking unit alone at any product ratio and will therefore always require less feedstock.

From the combined weight percents of the $C_2=/C_3=$ product for each run, it can be seen that in the integrated system, the combined $C_2=/C_3=$ product selectivity is not greatly affected by the product ratio, i.e. a selectivity of between about 83.8 and 84.5 weight % resulted at all three product ratios tested. In the cracking unit alone, however, total $C_2=/C_3=$ product selectivity varies with the $C_2=/C_3=$ product ratio, i.e., 61.8 weight % at a product ratio of 3.1 compared to about 70.0 weight % at a product ratio of 6.1, and about 67.8 weight % at a product ratio of 1.8.

The present integrated system, therefore, is not only advantageous over the prior art in that it can produce ethylene and propylene in higher selectivity, but also in that this high product selectivity is not significantly affected by the ethylene/propylene product ratio. Additionally, catalytic dehydrogenation of the propane fraction reduces or eliminates the need to hydrotreat the refined stream or the purified propylene product stream.

What is claimed is:

1. A process for producing ethylene and propylene in high selectivity from feed streams containing ethane and propane comprising:
   (a) separating a feed stream into an ethane fraction and a propane fraction, if not already separated;
   (b) passing said ethane fraction through a steam cracking unit at a temperature from about 750° to 930° C., thereby forming an ethylene-rich stream;
   (c) passing said propane fraction through a dehydrogeration unit over a suitable catalyst at a temperature from about 425° to 815° C., thereby forming a propylene-rich stream;
   (d) adjusting the pressure of said propylene-rich stream to about equal to that of said ethylene-rich stream;
   (e) combining said ethylene-rich and propylene-rich streams, thereby forming a combined ethylene/propylene stream;
   (f) initially compressing and cooling said combined ethylene/propylene stream, thereby removing impurities and by-products, and producing a refined stream;
   (g) subjecting said refined stream to low temperature fractionation to effect the recovery of ethylene and propylene and unreacted ethane and propane;
   (h) recycling said unreacted ethane and propane back to the steam cracking and dehydrogenation units respectively.

2. The process in accordance with claim 1 wherein said dehydrogenation unit employs a noble metal or metal oxide catalyst on a calcined support.

3. The process in accordance with claim 1 wherein at least about 80% of the initial combined ethane and propane feed is recovered as purified ethylene and propylene.

4. The process in accordance with claim 1 wherein the combined ethylene/propylene stream is hydrotreated during the compressing and cooling step.

5. The process in accordance with claim 1 wherein the refined stream is hydrotreated during the low temperature fractionation step.

* * * * *

UNITED STATES PATENT AND TRADEMARK OFFICE
CERTIFICATE OF CORRECTION

PATENT NO. : 4,458,096
DATED : July 3, 1984
INVENTOR(S) : David J. Phillips, et al It is certified that error appears in the above-identified patent and that said Letters Patent are hereby corrected as shown below:

Column 6, Line 16
Delete "geration" and substitute therefor -- genation --

Signed and Sealed this

Fifth Day of March 1985

[SEAL]

Attest:

DONALD J. QUIGG

Attesting Officer     Acting Commissioner of Patents and Trademarks